United States Patent
Brieden et al.

(12) 
(10) Patent No.: US 6,773,910 B1
(45) Date of Patent: Aug. 10, 2004

(54) METHOD OF PREPARING (S)- OR (R) -3,3,3-TRIFLUORO-2-HYDROXY-2-METHYLPROPIONIC ACID

(76) Inventors: Walter Brieden, Grundbielstrusse 9, Glis (CH), CH-3902; Andrew Naughton, Weingartenweg 16, Visp (CH), CH-3930; Karen Robins, St. Martinistrasse 3, Visp (CH), CH-3930; Nicholas Shaw, Weingartenweg 14, Visp (CH), CH-3930; Andreas Tinschert, Kronengasse 4, Brig (CH), CH-3900; Thomas Zimmermann, Furkastrasse 9, Naters (CH), CH-3904

( * ) Notice: Subject to any disclaimer, the term of this patent is extended or adjusted under 35 U.S.C. 154(b) by 0 days.

(21) Appl. No.: 09/214,679
(22) PCT Filed: Jul. 10, 1997
(86) PCT No.: PCT/EP97/03670

§ 371 (c)(1),
(2), (4) Date: Dec. 30, 1999

(87) PCT Pub. No.: WO98/01568
PCT Pub. Date: Jan. 15, 1998

(30) Foreign Application Priority Data

Jul. 10, 1996 (CH) .............................. 1723/96
Mar. 3, 1997 (CH) .............................. 500/97

(51) Int. Cl.$^7$ .......................... C12N 1/00; C12N 1/20; C12P 1/00; C12P 7/58; C12P 7/52
(52) U.S. Cl. ................ 435/243; 435/252.3 T; 435/252.31; 435/41; 435/137; 435/141; 435/262

(58) Field of Search ............. 435/41, 137, 141, 435/170, 243, 252.3 T, 252.31, 262, 120, 132, 135, 136, 183, 195, 252.3, 320.1

(56) References Cited

FOREIGN PATENT DOCUMENTS

| EP | 0356912 | 3/1990 |
| EP | 0433117 | 6/1991 |
| EP | 0524781 | 1/1993 |

OTHER PUBLICATIONS

Hirrlinger et al. J. Bacteriol., Jun. 1996, vol. 178(12):3501–3507.*
Hashimoto et al. Biochimica et Biophysica Acta, 1991, vol. 1088:225–233.*
Lieber et al., "The ultraviolet absorption spectra of 5–nitroaminotetrazole and its salts", J. Chem. Soc. 2329–2331 (May 1951).

* cited by examiner

*Primary Examiner*—Manjunath N. Rao
(74) *Attorney, Agent, or Firm*—Baker Botts L.L.P.

(57) ABSTRACT

Described are new micro-organisms and a new enzyme capable of using as sole source of nitrogen the propionic acid amide of formula (VI), in racemate form or as optically active isomers. Described also is a method of preparing (S)- or (R)-3,3,2-trifluoro-2-hydroxy-2-methylpropionic acid of formulas (I) and (II) starting from trifluoroaceto-acetic ester. The first three process steps are chemical, the fourth process step microbiological.

16 Claims, 7 Drawing Sheets sad "reading frame"

METHOD OF PREPARING (S)- OR (R) -3,3,3-TRIFLUORO-2-HYDROXY-2-METHYLPROPIONIC ACID

The present invention relates to a novel process for the preparation of (S)- or (R)-3,3,3-trifluoro-2-hydroxy-2-methylpropionic acid and to novel microorganisms capable of utilizing the propionamide of the formula

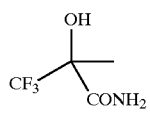

VI in the form of the racemate or of its optically active isomers as the sole nitrogen source.

(S)-3,3,3-Trifluoro-2-hydroxy-2-methylpropionic acid is an important intermediate for the preparation of therapeutic amides (EP-A 0 524 781).

In the following text, 3,3,3-trifluoro-2-hydroxy-2-methylpropionic acid is abbreviated to 2,2-HTFMPS, and 3,3,3-trifluoro-2-hydroxy-2-methyl-propionamide to 2,2-HTFMPA.

In J. Chem. Soc., 1951, p. 2329 there is described a process for the preparation of (S)-2,2-HTFMPS where the corresponding racemate is converted into the desired (S) enantiomer by means of dimethoxystrychnine. The disadvantage of this process is that dimethoxystrychnine, which is employed for the racemate resolution, is too expensive.

EP-A 0 524 781 describes a process for the preparation of (S)-HTFMPS, in which the corresponding racemate is converted into the desired (S) enantiomer by means of (S)-(−)-α-methylbenzylamine. The disadvantage of this process is that large amounts of (S)-(−)-α-methylbenzylamine must be employed, which, again, makes this process too expensive.

It is an object of the present invention to provide an inexpensive, technically feasible process for the preparation of (S)- or (R)-2,2-HTFMPS.

This object is achieved by the microorganisms according to claim 1 and claim 11 according to the invention, the polypeptides according to claim 4 and by the processes according to claims 15 and 16.

Accordingly, the present invention relates to microorganisms selected from the wild, so-called "wild types", enzyme extracts therefrom, enzymes isolated therefrom having stereospecific amidohydrolase activity, and DNA/DNA fragments which are isolated from the "wild types" and which encode a stereospecific amidohydrolase. The present invention furthermore relates to so-called genetically engineered microorganisms comprising these DNA fragments, or vectors. A further subject-matter is a process for the preparation of (S)- or (R)-2,2-HTFMPS and a process for the preparation of (S)- or (R)-2,2-HTFMPA using the above-described microorganisms.

The invention is illustrated in greater detail by the Figures below.

FIG. 1 shows the restriction map of the isolated DNA
FIG. 2 shows plasmid pPRS1b
FIG. 3 shows plasmid pPRS2a
FIG. 4 shows the pH optimum of the amidohydrolase
FIG. 5 shows the Michaelis-Menten kinetics of the amidohydrolase
FIG. 6 shows the temperature optimum of the amidohydrolase
FIG. 7 shows the effect of methanol on the amidohydrolase.

The "wild types" according to the invention can be isolated from soil samples, sludge or waste water with the aid of customary microbiological techniques. In accordance with the invention, the isolation is performed in such a way that these are cultured in the customary manner in a medium comprising the propionamide of the formula VI in the form of the racemate or one of its optically active isomers as the sole nitrogen source, together with a suitable carbon source. Then, those which are stable and which utilize the propionamide of the formula VI as the sole nitrogen source are selected from the culture obtained by culturing.

By way of suitable carbon sources, the "wild types" are capable of utilizing sugar, sugar alcohols or carboxylic acids as growth substrate. Examples of sugars which can be used are glucose, arabinose, rhamnose, lactose or maltose. Sugar alcohols which can be used are, for example, sorbitol, mannitol or glycerol. Citric acid is an example of a carboxylic acid which can be used. Glycerol or glucose is preferably employed as the carbon source.

The selection and growth media which can be used are those conventionally used in expert circles, such as, for example, a mineral salt medium as described by Kulla et al., Arch. Microbiol. 135, pp. 1–7, 1983.

It is expedient to induce the active enzymes of the microorganisms during growth and selection. The propionamide of the formula VI in the form of the racemate or one of its optically active isomers, acetamide or malonic diamide, can be used as the enzyme inductor.

Growth and selection normally take place at a temperature from 0 to 42° C., preferably from 20 to 37° C. and at a pH of 4 to 9, preferably at a pH of 6 to 8.

Preferred "wild types' are those of the genus Klebsiella, Rhodococcus, Arthrobacter, Bacillus and Pseudomonas which utilize propionamide (formula VI). Very especially preferred are microorganisms of the species *Klebsiella oxytoca* PRS1 (DSM 11009), *Klebsiella oxytoca* PRS1K17 (DSM 11623), Pseudomonas sp. (DSM 11010), *Rhodococcus opacus* ID-622 (DSM 11344). *Arthrobacter ramosus* ID-620 (DSM 11350), Bacillus sp. ID-621 (DSM 11351), *Klebsiella planticula* ID-624 (DSM 11354) and *Klebsiella pneumoniae* ID-625 (DSM 11355), and their functionally equivalent variants and mutants. The *Klebsiella oxytoca* (DSM 11009), *Klebsiella planticula* ID-624 (DSM 11354) and *Klebsiella pneumoniae* ID-625 (DSM 11355) "wild types" preferentially have (R)-amidohydrolase activity, and the Pseudomonas sp. (DSM 11010), *Rhodococcus opacus* ID-622 (DSM 11344), *Arthrobacter ramosus* ID-620 (DSM 11350) and Bacillus sp. ID-621 (DSM 11351) "wild types" preferentially have (S)-amidohydrolase activity. The microorganisms termed DSM 11010, DSM 11009 were deposited on 24.06.1996, the microorganisms termed DSM 11355, DSM 11354 on 27.12.1996, the microorganisms termed DSM 11351, DSM 11350 and DSM 11344 on 13.12.1996 and the microorganisms termed DSM 11623 on 20.06.1997 at the Deutsche Sammlung von Mikroorganismen und Zellkulturen GmbH, Mascheroderweg 1b, D-38124 Braunschweig in compliance with the Budapest Treaty.

"Functionally equivalent variants and mutants" of the "wild types" are to be understood as meaning strains which have essentially the same characteristics and functions as the original microorganisms. Such variants and mutants may be formed randomly, for example by UV irradiation, or in a directed fashion by chemical mutagenesis, for example by intercalating substances, such as acridine dyes.

Taxonomic Description of *Klebsiella oxytoca* PRS1 (DSM 11009)

| | |
|---|---|
| Cell shape | Rods |
| Width μm | 1.0–1.2 |
| Length μm | 1.2–2.0 |
| Motility | – |
| Gram reaction | – |
| Lysis by 3% KOH | + |
| Aminopeptidase (Cerny) | + |
| Spores | – |
| Oxidase | – |
| Catalase | + |
| Growth anaerobic | + |
| Gas from glucose | + |
| Acid from (ASA) | |
| Glucose | + |
| Fructose | + |
| Xylose | + |
| Erythritol | – |
| Adonitol | + |
| D-Mannose | + |
| L-Rhamnose | + |
| Inositol | + |
| Sorbitol | + |
| α-Methyl-D-glucoside | + |
| Cellobiose | + |
| Maltose | + |
| Lactose | + |
| D-Arabitol | + |
| ONPG | + |
| ADH | – |
| LDC | w |
| ODC | – |
| VP | + |
| Indole | + |
| H₂S generation | – |
| Simmons citrate | + |
| Urease | + |
| Methyl Red | – |
| Hydrolysis of | |
| Gelatin | – |
| DNA | – |
| Tween 80 | – |

Taxonomic Description of Pseudomonas sp. (DSM 11010)

| | |
|---|---|
| Cell shape | Rods |
| Width μm | 0.7–0.8 |
| Length μm | 1.5–3.5 |
| Motility | + |
| Gram reaction | – |
| Lysis by 3% KOH | + |
| Aminopeptidase (Cerny) | + |
| Spores | – |
| Oxidase | + |
| Fluorescence | + |
| Catalase | + |
| Growth at 41° C. | – |
| ADH | + |
| Urease | – |
| Hydrolysis of gelatin | + |
| Nitrate reduction | – |
| Denitrification | – |
| Levan from sucrose | + |
| Lecithinase | + |
| Substrate utilization | |
| Adipate | – |
| Citrate | + |
| Malate | + |
| L-Mandelate | – |
| Phenyl acetate | – |
| D-Glucose | + |
| Maltose | – |

-continued

| | |
|---|---|
| Trehalose | + |
| Mannitol | + |
| Adonitol | + |
| Acetamide | + |
| Hippurate | – |
| Tryptamine | – |
| Butylamine | – |

Abbreviations:
ASA: acetylsalicylic acid
ONPG: O-Nitro-phenylgalactosidase
ADH: Alcohol dehydrogenase
LDC: Lactate decarboxylase
ODC: Ornithin decarboxylase
VP: Voges Proskauer The enzyme according to the invention which has stereospecific amidohydrolase activity can be obtained, for example, from the "wild types" which have already been described and are capable of hydrolysing the propionamide of the formula

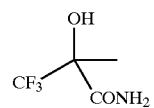

VI in the form of the racemate or its (R) isomers, and functionally equivalent variants and mutants thereof.

"Functionally equivalent variants and mutants" of the enzymes are to be understood as meaning enzymes which essentially have the same characteristics and functions. Such variants and mutants can be formed randomly, for example by mutation.

The enzyme is expediently characterized by a) a pH optimum of pH 10±0.5 b) a temperature optimum of between 65 and 70° C. at a pH of 10 and c) a $K_M$ value for the substrate (R)-2,2-HTFMPA of 32 mM (60° C. in 100 mM CAPS buffer (3-(cyclohexylamino)-1-propanesulphonic acid) pH 10), in particular in that d) a methanol concentration of 5 to 20% has an inhibitory effect and e) The N-terminal amino acid sequence is: Met-Lys-Trp-Leu-Glu-Glu-Ser-Ile-Met-Ala-Lys-Arg-Gly-Val-Gly-Ala-Ser-Arg-Lys-Pro (SEQ ID NO: 3).

This stereospecific amidohydrolase can be isolated from the above-described "wild types" which are capable of utilizing the propionamide of the formula VI in the form of the racemate or of its R isomer as the sole nitrogen source. The amidohydrolase is expediently isolated from the "wild types" of the genus Klebsiella, preferably from *Klebsiella oxytoca* PRS1 (DSM 11009) or *Klebsiella oxytoca* PRS1K17 (DSM 11623).

Naturally, this enzyme may also be isolated from the genetically engineered microorganisms which are derived from these "wild types".

To obtain the stereospecific amidohydrolase, the "wild types" are grown (cultured) in the customary manner in an aqueous nutrient medium comprising a carbon source, a nitrogen source, mineral salts and a vitamin source. The "wild types" are expediently cultured at a temperature from 20 to 35° C. and a pH of 6 to 8. The enzyme can then be isolated by enzyme purification methods known per se after cell disruption, for example using the French press.

The DNA according to the invention, or the DNA fragments according to the invention, which encode a stereospecific amidohydrolase as it is shown, in particular, by the amino acid sequence in SEQ ID No. 2 and which are characterized by the restriction map as shown in FIG. 1 and, in particular, by the nucleotide sequence in SEQ ID No. 1, also embrace their functionally equivalent genetic variants and mutants, i.e. genes which are derived from the genes of the wild-type organisms and whose gene products are essentially unmodified with regard to their biological function. The functionally equivalent genetic variants and mutants thus embrace, for example, base exchanges within the scope of the known degeneration of the genetic code, as they can be generated, for example, artificially to adapt the gene sequence to the preferred codon usage of a particular microorganism in which expression is to take place. The genetic variants and mutants also embrace deletions, insertions and substitutions of bases or codons, as long as the gene products of genes modified in this way remain essentially unaltered with regard to their biological function. This embraces, for example, gene sequences which exhibit a high level of homology to the wild-type sequences, for example greater than 70%, and which are capable of hybridizing with the complement of the wild-type sequences under stringent hybridization conditions, for example at temperatures between 60 and 70° C. and at a salt content of 0.5 to 1.5 M, in particular at a temperature of 67° C. and a salt content of 0.8 M.

The above-described "" wild types" which are employed as starting material for isolating the stereospecific amidohydrolase according to the invention may be employed as starting material for the DNA according to the invention.

The intact genes, or the intact DNA fragments according to the invention, can be isolated by known methods starting from a gene library for suitable microorganisms, such as *Klebsiella oxytoca*, from which the amidohydrolase gene, or fragments thereof, can be isolated and cloned in a known manner by hybridization with labelled oligonucleotides which contain sub-sequences of the amidohydrolase genes. The amidohydrolase gene will be abbreviated to sad hereinbelow.

To improve transcription, the sad gene is advantageously placed under the control of a strong promoter. The choice of promoter depends on the desired expression conditions, for example on whether constitutive or induced expression is desired, or on the microorganism in which expression is to take place.

Suitable promoters are the promoters $P_L$ and $P_R$ of phage lambda (cf. Schauder et al., Gene, 52, 279–283, 1987), the $P_{trc}$ promoter (Amann et al., Gene, 69, 301–315, 1988), the promoters $P_{Nm}$, $P_{Sl}$ (M. Labes et al., Gene, 89, 37–46, 1990), the $P_{trp}$ promoter (Amann et al., Gene, 25, 167–178, 1983), the $P_{lac}$ promoter (Amann et al., Gene, 25, 167–178, 1983) and the $P_{tac}$ promoter, a hybrid of the abovementioned $P_{trp}$ and $P_{lac}$ promoters, which can be employed as constitutive or inducible promoters (Russel and Bennett, Gene, 20, 231–243, 1982). The $P_{lac}$ promoter is preferably used.

For use in the production of, for example, (R)-2,2-HTFMPS in a suitable production strain, the DNA fragments according to the invention are expediently incorporated into suitable known vectors, preferably expression vectors, with the aid of known techniques. Autonomously and self-replicating plasmids or integration vectors may be used as vectors.

Depending on the type of vector chosen, the sad genes can be expressed in a variety of microorganisms. Suitable vectors are both vectors with a specific host range and vectors with a broad host range. Examples of vectors with a specific host range, for example for *E. coli*, are pBR322 (Bolivar et al., Gene, 2, 95–113), the commercially available pBLUESCRIPT-KS+®, pBLUESCRIPT-SK+® (Stratagene), pUC18/19 (Yanisch-Perron et al., Gene 33, 103–119, 1985), pK18/19 (Pridmore, Gene, 56, 309–312, 1987), pRK290X (Alvarez-Morales et al., Nucleic Acids Research, 14, 4207–4227) and pRA95 (available from Nycomed Pharma A S, Huidove, Denmark). pBLUESCRIPT-KS+® is preferably employed.

All vectors which are suitable for Gram-negative bacteria may be employed as broad host-range vectors.

Examples of such broad host-range vectors are pRK290 (Ditta et al., PNAS, 77, 7347–7351, 1980) or their derivatives, pKT240 (Bagdasarian et al., Gene, 26, 273–282, 1983) or its derivatives, pGSS33 (Sharpe, Gene, 29, 93–102, 1984), pVK100 (Knauf and Nester, Plasmid, 8, 45–54, 1982) and its derivatives, pME285 (Haas and Itoh, Gene, 36, 27–36, 1985) and its derivatives.

For example the plasmids pPRS1b (FIG. 2), pPRS2a (FIG. 3), pPRS4 and pPRS7 were obtained in this manner.

To generate the production strains for fermentation, i.e. strains which can be employed for the preparation of, for example, (R)-2,2-HTFMPS, the vectors or DNA fragments according to the invention must be introduced into the desired host strains which are suitable for expression. To this end, the microorganisms are expediently transformed with the vectors containing the DNA fragments according to the invention in the customary manner which is known pet se. Then, the microorganisms can contain the DNA fragment according to the invention either on a vector molecule or integrated in their chromosome.

Suitable host strains, preferably strains with a high substrate and starting material tolerance are, for example, microorganisms of the genus Pseudomonas, Comamonas, Bacillus, Rhodococcus, Acinetobacter, Rhizobium, Agrobacterium, Rhizobium/Agrobacterium or Escherichia, the latter ones being preferred. Especially preferred are the microorganisms *Escherichia coli* DH5, *Escherichia coli* XL1-Blue® and *Escherichia coli* XL1-Blue MRF'®. Examples of suitable production strains are thus microorganisms of the species *Escherichia coli* DH5 and *Escherichia coli* XL1-Blue MRF'®, each of which contains plasmid pPRS1b, pPRS2a, pPRS4 or pPRS7.

The microorganism Escherichia coli XL1-Blue MRF'®/ pPRS2a was deposited as DSM 11635 on 30.06.1997 at the Deutsche Sammlung für Mikroorganismen und Zellkulturen GmbH, D-38124 Braunschweig, Mascheroderweg 1b in compliance with the Budapest Treaty.

The transformed host strains (production strains) can be isolated from a selective nutrient medium supplemented with an antibiotic to which the strains are resistant due to a marker gene located on the vector or the DNA fragment.

The process according to the invention for the preparation of (S)- or (R)-2,2-HTFMPS of the formulae

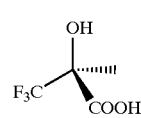

I

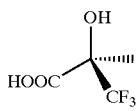

and/or of (R)- or (S)-2,2-HTFMPA of the formulae

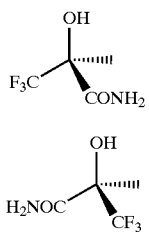

comprises the conversion of the propionamide of the formula

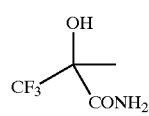

by means of the above-described microorganisms according to the invention, or by means of the enzymes isolated therefrom which exhibit stereospecific amidohydrolase activity.

The process for the preparation of (R)-2,2-HTFMPS and/or of (S)-2,2-HTFMPA is expediently carried out using the "wild types" of the genus Klebsiella, preferably of the species Klebsiella oxytoca PRS1 (DSM 11009), Klebsiella oxytoca PRS1K7 (DSM 11623), Klebsiella planticula ID-624 (DSM 11354), Klebsiella pneumoniae ID-625 (DSM 11355), using the genetically engineered microorganisms derived from these "wild types" or using the enzyme having a stereospecific amidohydrolase activity.

The process for the preparation of (S)-2,2-HTFMPS and/or (R)-2,2-HTFMPA is expediently carried out using the "wild types" of the genus Pseudomonas, Rhodococcus, Arthrobacter or Bacillus, in particular the species Pseudomonas sp. (DSM 11010), Rhodococcus opacus ID-622 (DSM 11344), Arthrobacter ramosus ID-620 (DSM 11350) and Bacillus sp. ID-621 (DSM 11351).

The biotransformation can be performed on dormant cells (non-growing cells which no longer require a carbon and energy source) or on growing cells, after having grown the microorganisms in the customary manner. The biotransformation is preferably carried out on dormant cells.

Media conventionally used by those skilled in the art may be employed for the biotransformation, such as, for example, phosphate buffers of low molarity, HEPES buffers, or the above-described mineral salt medium.

The biotransformation is expediently carried out with the single or continuous addition of propionamide (formula VI) in such a way that the concentration does not exceed 10% by weight, preferably 2.5% by weight.

The pH of the medium can range from 4 to 10, preferably from 5 to 9.5. The biotransformation is expediently carried out at a temperature of 10 to 60° C., preferably 20 to 40° C.

The resulting (S)- or (R)-2,2-HTFMPS, or (S)- or (R)-2,2-HTFMPA, respectively, can be isolated by customary work-up methods, such as, for example, by extraction.

The yield of (S)- or (R)-2,2-HTFMPS, or (S)- or (R)-2,2-HTFMPA, respectively, can be improved further in the customary manner by varying the nutrients in the medium and by adapting the fermentation conditions to the microorganism in question.

If appropriate, the (S)- or (R)-2,2-HTFMPA is hydrolysed to give the corresponding acid, either chemically in the presence of a base or microbiologically using microorganisms of the genus Rhodococcus.

An alkali metal hydroxide may be employed as the base. Sodium hydroxide or potassium hydroxide is expediently employed as the alkali metal hydroxide.

The microbiological hydrolysis is expediently carried out using microorganisms of the species Rhodococcus equi, Rhodococcus rhodochrous or Rhodococcus sp. S-6, preferably using microorganisms of the species Rhodococcus equi TG 328 (DSM 6710) or its functional equivalent variants and mutants. The microorganism Rhodococcus equi TG 328 is described in U.S. Pat. No. 5,258,305 and was deposited on 13.09.1991 at the Deutsche Sammlung von Mikroorganismen und Zellkulturen GmbH, D-38124 Braunschweig, Mascheroderweg 1b in compliance with the Budapest Treaty. Normally, these microorganisms are grown by the method of Gilligan et al. (Appl. Microbiol. Biotech., 39, 1993, 720–725) before the actual microbiological hydrolysis is carried out. In principle, the microbiological hydrolysis is effected by methods conventionally used in the art. The hydrolysis is expediently effected at a temperature of 20 to 40° C. and a pH of 6 to 9.

The propionamide of the formula

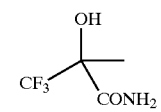

is prepared in such a manner that, in a first step, trifluoroacetate of the formula

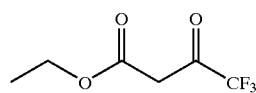

is first converted into trifluoroacetone of the formula

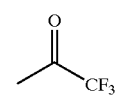

using a mineral acid.

Examples of a mineral acid which can be employed are hydrochloric acid, sulphuric acid, nitric acid or phosphoric acid. Acids which are preferably employed are sulphuric acid, phosphoric acid or nitric acid, in particular sulphuric acid.

The first step of the reaction is expediently carried out in a polar protic solvent such as, for example, in a lower alcohol, in water or in a mixture of lower alcohol/water. Lower alcohols which can be employed are, for example, methanol, ethanol, propanol, isopropanol, butanol, tert-butanol or isobutanol.

The first step of the reaction is expediently carried out at a temperature of 50 to 100° C., preferably at a temperature of 70 to 95° C.

In the second step of the process according to the invention, trifluoroacetone (formula IV) is reacted with a cyanide to give the propionitrile of the formula

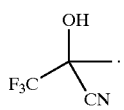

V

Cyanides which are expediently employed are alkali metal cyanides such as sodium cyanide or potassium cyanide, preferably sodium cyanide.

The second step of the reaction is expediently carried out in the presence of a mineral acid. Suitable mineral acids are those which have been described above. The preferred mineral acid is sulphuric acid. Normally, an excess of mineral acid is employed, based on trifluoroacetone. It is preferred to use 1 to 10 mol of mineral acid per mole of trifluoroacetone. The solvents which can be used are the same as in the first step.

The second step is expediently carried out at a temperature of −20 to 100° C., preferably 0 to 20° C.

In the third step of the process according to the invention, the propionitrile of the formula V is converted into the propionamide of the formula VI, either chemically in a concentrated mineral acid or microbiologically using mutated microorganisms of the genus Rhodococcus.

Mineral acids which can be employed are the same as in the first and second step. A "concentrated mineral acid" is to be understood as meaning hereinbelow a 30 to 100% strength mineral acid. A 75 to 100% strength, preferably a 90 to 100% strength, mineral acid is expediently used in the third step. The chemical reaction in the third step is expediently carried out at a temperature of 0 to 160° C., preferably 70 to 120° C.

The mutated microorganisms of the genus Rhodococcus no longer contain amidase and are thus no longer capable of converting an amide into the corresponding acid. The mutation can be effected by customary methods (J. H. Miller, Experiments in Molecular Genetics, Cold Spring Harbor Laboratory, 1972, p. 24). Expedient mutation methods are the frameshift method, the deletion method or the transposon insertion method.

Suitable microorganism species for the mutation are *Rhodococcus equi, Rhodococcus rhodochrous* or Rhodococcus sp. S-6. It is preferred to mutate the above-described *Rhodococcus equi* TG 328 (DSM 6710), thus obtaining *Rhodococcus equi* TG 328-2 (DSM 11636) and its functionally equivalent variants and mutants. The microorganism TG 328-2 was deposited on 30.06.1997 at the Deutsche Sammlung für Mikroorganismen und zellkulturen GmbH, D-38124 Braunschweig, Mascheroderweg 1b in compliance with the Budapest Treaty. This microorganism is cultured under the same conditions as the unmutated microorganisms which have already been described above.

(R)- and (S)-2,2-HTFMPA are compounds hitherto not described in the literature and therefore also part of the invention. They can be employed as novel intermediates for the preparation of (R)- or (S)-2,2-HTFMPS, for example by hydrolysis in the presence of a base.

EXAMPLE 1

Preparation of Trifluoroaceton 500 g (4.9 mol) of concentrated sulphuric acid (96% strength; Merck) were added to 1 l of distilled water, and the mixture was heated to 73° C. Then, 500 g (2.69 mol) of trifluoroacetate were added slowly, during which process two phases formed. The batch was heated to reflux temperature, and the trifluoroacetone formed in the process was distilled off. After 2 hours, 293.8 g of trifluoroacetone were isolated as colourless liquid, corresponding to a yield of approx. 90%. GC analysis revealed a purity of 92.1%.

EXAMPLE 2

Preparation of 2-hydroxy-2-methyl-3,3,3-trifluoromethylpropionitrile 39.4 g of sodium cyanide (0.763 mol) were added to 174 ml of distilled water and the mixture was cooled to −1° C. 100 g of trifluoroacetone (0.822 mol) were subsequently added dropwise, during which process the temperature of the reaction mixture climbed to 6° C. After addition of trifluoroacetone had ended, 293.4 g of 6 N sulphuric acid (1.4916 mol of H) were added at 4–5° C. The reaction mixture was then stirred overnight at room temperature. The batch was subsequently extracted with ethyl acetate or with tert-butyl methyl ether and the combined organic phases were distilled either under atmospheric pressure at 32° C. or under slightly subatmospheric pressure (300–120 mbar). In total, 88 g of product of 91.2% purity (measured by GC) were obtained, which corresponds to a yield of 75.6%.

EXAMPLE 3 a) Chemical Preparation of (R,S)-2,2-HTFMPA

98% strength sulphuric acid was introduced into the reaction vessel under argon atmosphere. 15 g of 2-hydroxy-2-methyl-3,3,3-trifluoromethylpropionitrile (86.9% according to GC) were added to this, and the reaction mixture was heated to 95° C. After the addition of starting material, the reaction mixture was heated for 15 minutes at 114° C. The reaction mixture was then cooled to 5° C., during which process a viscous brown solution formed. 40 g of distilled water were subsequently added dropwise. During this process, care was taken that the temperature of the reaction mixture did not exceed 15° C. The yellowish suspension formed in this process was cooled for 15 minutes at −15° C. and then filtered. The filter cake was washed with 20 ml of ice-cold water and then dried in vacuo. This gave 12.64 g of a pale yellowish crude product. The crude product was subsequently refluxed in 13 ml of ethyl acetate and then cooled to room temperature. This suspension was treated with 15 ml of hexane, and the mixture was cooled to 0° C. The mixture was then washed once more with hexane. Drying in vacuo gave 11.8 g of product, which corresponds to a yield of 80.2%.

M.p.: 143.1–144.3° C.

b) Microbiological Production of (R,S)-2,2-HTFMPA (Using a Mutated Microorganism of the Genus Rhodococcus)

For mutation purposes, *Rhodococcus equi* TG 328 was incubated by standard methods overnight in "nutrient broth" at 30° C. with added acridine ICR 191. The cells were then harvested and washed using 0.9% strength NaCl solution. The cells were then incubated in fresh medium overnight at 30° C.

The mutated cells were selected in a mineral salt medium described by Gilligan et al. (Appl. Microbiol. Biotech., 39, 1993, 720–725) in the presence of fluoroacetamide as counterselective agent. This counterselective agent only destroys growing bacteria. Mutants, which no longer contain amidase and no longer grow on (R,S)-2,2-HTFMPA survive and are concentrated. The cells were subsequently harvested, washed with 0.9% strength NaCl solution, incubated overnight in fresh medium and then plated out. The colonies were tested for nitrile hydratase activity. The frequency of the desired mutation was 2%.

The mutant of *Rhodococcus equi* TG 328-2 was grown in a mineral salt medium as described by Gilligan et al., (ibid). The washed cells were incubated at $OD_{650\,nm}$=5.0, both with 2-hydroxy-2-methyl-3,3,3-trifluoromethylpropionitrile solution (1% strength) and with a (R,S)-2,2-HTFMPA solution (1% strength) in 100 mM phosphate buffer (pH 7.7) at 37° C. After 16 hours, GC analysis demonstrated that the nitrile was converted quantitatively into the amide, whereas the amide was not hydrolysed to give the acid.

EXAMPLE 4

Production of (S)-2,2-HTFMPA and (R)-2,2-HTFMPS by Means of a Microorganism Containing an Amidohydrolase (Wild Type)

4.1. Selection and Isolation of Microorganisms with (R)- and (S)-amidase Activity 100 ml of phosphate buffer (0.1 M, pH 7.0) were added to a soil sample of 10 g, and the mixture was left to stand for 10 minutes and filtered. Then, the supernatant (5.0 ml) or 1 ml of waste water (ARA, Visp) was subcultured in a mineral salt medium (25 ml; Kulla et al., Arch. Microbiol. 135, pp. 1–7, 1983) containing glycerol and (R,S)-HTFMPA (carbon/nitrogen ratio 5:1). This culture was subsequently incubated until a mixed culture had formed which can utilize (R)- and/or (S)-2,2-HTFMPA as the sole nitrogen source. This culture was then subcultured repeatedly and incubated at 30° C. until a mixed culture had formed.

The pure culture of these microorganisms was maintained with the aid of traditional microbiological techniques.

The resulting microorganism strains were then tested on agar plates for growth on (R,S)-2,2-HTFMPA. The positive strains were tested further. These strains were then used to inoculate a preculture medium. The microorganisms contained in this preculture were transferred into the mineral salt medium and then tested for their capability of selectively utilizing (R)-2,2-HTFMPA and/or (S)-2,2-HTFMPA as sale nitrogen source, the supernatant being checked by GC for (R)-2,2-HTFMPS or (S)-2,2-HTFMPS formation and for the concentration of one of the two amide enantiomers.

4.2. Determination of (R)- or (S)-2,2-HTFMPA Amidohydrolase Activity

To determine the hydrolase activity, the microorganism suspension was brought to an optical density of 4.0 at 650 nm. A phosphate buffer (100 mmolar), pH 7.0, supplemented with 0.5% by weight of (R,S)-HTFMPA, acted as the medium. This suspension was incubated for 2 hours at 30° C. with shaking. The $NH_4^+$ liberated by the hydrolase was determined either calorimetrically or by means of an ammonium electrode, and the HTFMPA was measured by GC. The activity was expressed as g of (R)- or (S)-HTFMPA converted/l/h/optical density at 650 nm, with the proviso that 1 mmol of $NH_4^+$ formed equals 1 mmol of converted HTFMPA.

TABLE 1

Hydrolase activity of Klebsiella and Pseudomonas

| Strain | Hydrolase activity | |
|---|---|---|
| | (R)-specific | (S)-specific |
| | (g/1/h/O.D. 650 nm) | |
| DSM 11009 (*Klebsiella oxytoca* PRS1) | 0.11 | — |
| DSM 11010 (*Pseudomonas* sp.) | — | 0.09 |

4.3. Production of (S)-2,2-HTFMPA and (R)-2,2-HTFMPS.

*Klebsiella oxytoca* PRS1 (DSM 11009), *Klebsiella planticula* ID-624 (DSM 11354) or *Klebsiella pneumoniae* ID-625 (DSM 11355) were incubated for 2 days at 30° C. on mineral salt medium agar plates with glycerol as carbon source and (R,S)-2,2-HTFMPA as sole nitrogen source. The composition of the mineral salt medium is described in Kulla et al., Arch. Microbiol., 135, pp. 1–7, 1983. These plated microorganisms were used to incubate a preculture medium of the same composition which was incubated for 2 days at 30° C. The same mineral salt medium (600 ml) was inoculated with 50 ml of preculture for induction and biomass production and incubated at 30° C. for 21 hours. The cells were subsequently harvested by centrifugation and taken up in 0.1 M phosphate buffer pH 7.0. After resuspending the cells in 0.05 M phosphate buffer (500 ml, pH 8.0), an optical density at 650 nm of 10 was established, and 1.0% by weight of (R,S)-2,2-HTFMPA was added. After incubation for approx. 5.5 hours at 40° C., (R)-2,2-HTFMPA was converted completely into the corresponding acid, which corresponds to an optical purity (ee) of 100% and a yield of 48%.

The course of the reaction was monitored on the basis of $NH_4^+$ liberation and GC analysis of the supernatant.

4.4. Production of (S)-2,2-RTFMPS and (R)-2,2-HTFMPA Using a Microorganism Containing an (S)-amidohydrolase The microorganisms *Pseudomonas* sp. (DSM 11010), *Rhodococcus opacus* ID-622 (DSM 11344), *Arthrobacter ramosus* ID-620 (DSM 11350) and *Bacillus* sp. ID-621 (DSM 11351) were isolated analogously to Example 4.1. The induction period was 2 days, and all the other conditions were the same as in Example 4.3.

In contrast to Example 4.3., the bio-transformation using these microorganisms was carried out with 0.5% by weight of (R,S)-2,2-HTFMPA. The strain *Pseudomonas* sp. (DSM 11010) has an (S)-specific hydrolase, and the activity of the hydrolase at pH 6.0 was determined as 0.09 g of (S)-2,2-HTFMPA (ee=86%), converted/l/h/O.D. 650 nm.

4.5. Work-up of (S)-2,2-HTPMPA and (R)-2,2-HTFMPS
a) By Means of Extraction 196 ml of a reaction mixture containing (S)-2,2-HTFMPA and (R)-2,2-HTFMPS (obtained from Example 4.3), 0.1 M phosphate buffer (250 ml), pH 10 were extracted 3 times with ethyl acetate (200 ml). The combined organic phases were dried with $Na_2SO_4$ and then evaporated at 40° C. and 50 mbar. This gave 912 mg of moist product. This product was dissolved in hot ethyl acetate (1.3 ml) and the solution was then cooled to room temperature. Addition of hexane (2 ml) resulted in precipitation of the product. The mixture was cooled to 0° C., and the product was filtered off and then dried in vacuo at 50° C. This gave 791 mg of (S)-2,2-HTFMPA, which corresponds to a yield of 78.2% based on half of the quantity employed. Only the (S) isomer was identified by means of chiral GC analysis. The remaining aqueous phase was brought to pH 1 with concentrated HCl and then extracted twice with ethyl acetate (200 ml). The extracts were evaporated at 40° C. and then dried. 1 ml of toluene was then added, and the mixture was cooled to room temperature. A further 2 ml of hexane were added, and the mixture was cooled to 0° C. The solid was washed 2–3 times with hexane and then dried. In total, 664 mg of (R)-2,2-HTFMPS were obtained from the aqueous phase after drying in vacuo at 35° C., which corresponds to a yield of 65.7% based on half of the amount employed. Only the (R) isomer was identified by means of chiral GC analysis.

b) By Means of Electrodialysis (Direct Isolation of (S)-2,2-HTFMPS)

A reaction mixture containing (S)-2,2-HTFMPA and (R)-2,2-HTFMPS (obtained from Example 4.3) was subjected to ultrafiltration to remove cellular material. The resulting solution was subjected to electrodialysis. (R)-2,2-HTFMPS and all buffer salts migrated through the membrane. After, electrodialysis had ended, a solution of pure (S)-2,2-HTFMPA (2342.2 g) was obtained. This solution was distilled at 135° C. and 20 mbar, until 447 g of product were obtained. 32.7 g of solid NaOH (0.8 mol) were then added, and the reaction mixture was refluxed for 3 hours. After this time, the (S)-2,2-HTFMPA had been converted completely into (S)-2,2-HTFMPS. The solution was cooled to a temperature of below 25° C., and the pH was brought from 13.8 to 1.0 using 93.6 g of concentrated HCl. The aqueous phase was extracted twice with ethyl acetate (500 ml). The combined organic phases were dried with $Na_2SO_4$ and then filtered. The solution was concentrated on a rotary evaporator until a viscous suspension was obtained. This suspension was treated twice with 20 ml of toluene each time, whereupon the resulting suspension was reconcentrated. A further 10 ml of toluene were then added, whereupon the mixture was refluxed. The solution was cooled to room temperature and treated with hexane (30 ml), until the product precipitated. The suspension was cooled to –10° C. and the product was collected by means of ultrafiltration. Drying in vacuo (temperature<35° C.) gave 14.1 g (0.0892 mol) of pure (S)-2,2-HTFMPS (ee value 99.7%), which corresponds to a yield of 35% (calculated on the basis of half the starting material).

EXAMPLE 5 a) Chemical Hydrolysis of (S)-2,2-HTFMPA to (S)-2,2-HTFMPS 0.47 g of sodium hydroxide (11.6 mmol) were added to 5 ml of distilled water. 650 mg (4.14 mmol) of (S)-2,2-HTFMPA were added to this, and the mixture was refluxed. After 2 hours, the reaction mixture was cooled to room temperature and the pH was brought to 1.0 using 10% strength HCl. The mixture was subsequently extracted twice with ethyl acetate (10 ml). The combined organic phases were dried over $Na_2SO_4$, filtered and evaporated at not more than 40° C. Drying in a vacuum oven (45 minutes at 35° C.) gave 618 mg of (S)-2,2-HTFMPS, which corresponds to a yield of 94.4%. Only the one isomer was identified by means of chiral GC analysis.

b) Microbiological Hydrolysis of (S)-2,2-HTFMPA to (S)-2,2-HTFMPS

*Rhodococcus equi* TG 328 (DSM 6710) were grown in a mineral salt medium as described by Gilligan et al., (ibid). The washed cells at $OD_{650\ nm}$=5.0 were incubated at 37° C. with an (S)-2,2-HTFMPA solution (1% in 100 mM phosphate buffer, pH 7.7). After 16 hours, GC analysis revealed that the (S)-2,2-HTFMPA had been converted quantitatively into (S)-2,2-HTFMPS.

EXAMPLE 6

6.1 Generation of a Capsule-negative Mutant of *Klebsiella oxytoca* PRS1

*Klebsiella oxytoca* PRS1 formed a slime capsule which conferred unfavourable characteristics on the strain during fermentation. A capsule-negative strain was advantageous for cell separation and subsequent work-up.

Capsule-negative mutants were isolated by means of acridine ICR 191 (J. H. Miller Experiments in Molecular Genetics, Cold Springs Harbor, 1972) as described below.

*Klebsiella oxytoca* PRS1 was inoculated into mineral salt medium containing 0.2% of glucose in the presence of acridine ICR 191 and incubated overnight at 30° C. This culture was subsequently subcultured in fresh medium and again incubated overnight at 30° C. The culture was diluted and plated onto nutrient agar. Non-slimy colonies were picked and checked. The mutants were isolated at a frequency of 0.18%. An example of such a mutant is *Klebsiella oxytoca* PRS1K17 (DSM 11623). This mutant shows the same growth behaviour as the wild type. The (R)-specific enzyme has the same activity as in *Klebsiella oxytoca* PRS1, but the strain does not form a slime capsule. This mutant was used for enzyme characterization and gene cloning.

6.2 Preparation of Chromosoaal DNA of *Klebsiella oxytoca* PRS1K17 (Capsule-negative Mutant of PRS1)

The chromosomal DNA of a fresh overnight culture of *Klebsiella oxytoca* PRS1K17 (100 ml nutrient yeast broth, 30° C.) was isolated by the modified method of R. H. Chesney et al. (J. Mol. Biol., 130, 1979), 161–173):

The cells which had been harvested by centrifugation (15 min, 6500×g, 4° C.) were resuspended in Tris buffer (2.25 ml, 0.05 mol/l, pH 8.0, 10% (w/v) sucrose).

After addition of 375 µl of lysozyme solution (10 mg/ml; 0.25 mol/l Tris HCl buffer, pH 8.0) and 900 µl of 0.1 mol/l EDTA, pH 8.0, the suspension was cooled for 10 minutes on ice. Thereupon, 450 µl of 5% (w/v) SDS and 50 µl of ribonuclease (10 mg/ml $H_2O$) were added and the mixture was incubated for 30 minutes at 37° C. Incubation was continued for 2 hours after addition of a spatula-tipful of proteinase K and 400 µl of pronase (20 ml/ml $H_2O$). After mixing with 4.3 g of CsCl, the mixture was centrifuged (30 min, 40,000×g, 20° C.), treated with 250 µl of ethidium bromide (10 mg/ml), and the mixture was centrifuged in an ultracentrifuge (Vti 62.5 tubes; more than 8 hours, 246,000× g, 20° C.). The DNA band was drawn off from the tube under long-wave UV light. After adding 4 volumes of TE buffer (10 mmol/l Tris HCl, pH 8.0, 1 mmol/l EDTA), the ethidium bromide was extracted three times with water-saturated n-butanol. The DNA was precipitated with isopropanol, taken up in TE buffer and incubated for 15 minutes at 65° C. The material was capable of being stored at 4° C.

6.3 Restriction and Ligation of the Chromosomal DNA

5 µg of *Klebsiella oxytoca* PRS1K17 DNA and 4.5 µg of vector DNA (pBLUESCRIPT-KS+®) were cleaved with 20 units of restriction enzyme HindIII each in a total restriction buffer volume of 100 µl (6.5 hours at 37° C.). The DNAs were precipitated with ethanol and dried in the Speed Vac$^R$ concentrator. The precipitates were taken up in the ligation buffer (20 mmol/l Tris buffer, 10 mmol/l DTT (dithiothreitol), 10 mmol/l $MgCl_2$, 0.6 mol/l ATP (adenosin triphosphate, pH 7.2) and combined (ligation volume 100 µl).

After addition of 1 unit of T4 DNA ligase, the mixture was incubated overnight at 13° C. The DNA of the ligation mixture was precipitated with isopropanol and taken up in 30 µl of water for transformation.

6.4 Transformation of *E. coli* XL1-Blue MRF'® and Selection

Competent *E. coli* XL1-Blue MRF'® cells were transformed with the ligation mixture by electroporation following the method described by S. Fiedler and R. Wirth (Analyt. Biochem., 170, 1988, 38–44).

To detect plasmid, selection was performed on nutrient agar with ampicillin (100 µg/ml) and to detect "insert", selection was performed with 0.5 mmol/l IPTG (isopropyl-β-D-thiogalactoside) and X-Gal (30 µg/ml, 5-bromo-4-chloro-3-indolyl-β-D-galactopyranoside) during incubation at 37° C.

At a transformation frequency of $1.7 \times 10^8$ cfu/ml ("colony-forming units" Δlive cells), virtually all clones carried a HindIII "insert".

EXAMPLE 7

Screening of the *Klebsiella oxytoca* PRS1K17 Gene Library for the (R)-specific Amidohydrolase Gene Clones carrying hybrid plasmids (HindIII "insert") were checked for their ability to grow on minimal medium agar as described by H. Kulla et al. (Arch. Mikrobiol., 135, 1983, 1–7) with 0.4% (v/v) glycerol as the C source, 0.2% (w/v) of (R,S)-2,2-HTFMPA as the sole N source and ampicillin (5 µg/ml) for plasmid stabilization. Only clones which contained the intact amidohydrolase gene sad on the DNA "insert" in the plasmid were capable of utilizing (R,S)-HTFMPA as N source, converting the former into the desired (R)-acid and growing on this minimal medium. All clones which were selected in this manner contained a hybrid plasmid of vector pBLUESCRIPT-KS+® with a HindIII "insert" of approx. 2.73 kb.

This allowed identification of strain *E. coli* XL1-Blue MRF'® with the plasmid termed pPRS2a, from which plasmid pPRS2a was isolated and characterized in greater detail.

EXAMPLE 8

Localization of the Amidobydrolase Gene (Sad) on the Cloned HindIII Fragment 8.1 Restriction Map of pPRS2a A coarse restriction map of pPRS2a as regards XhoI, DraII, SmaI, PstI, SalI, BamHI was established by restriction analysis following conventional procedures (Current Protocols Molecular Biology, John Wiley and Sons, New York, 1987, Section 2). The restriction map is shown in FIG. 1.

8.2 Formulation of Mixed DNA Oligomers Based on the Amidohydrolase N-terminal Peptide Sequence The genetic code allowed the formulation, and synthesis using a DNA synthesizer, of a mixed DNA oligomer for the following *Klebsiella oxytoca* PRS1K17 amidohydrolase N-terminal peptide sequence:

| 5' | CAK | CAK | CTN | ACN | GAR | GAR | ATG | CA 3' |
|----|-----|-----|-----|-----|-----|-----|-----|-------|
| AS | His | His | Leu | Thr | Glu | Glu | Met |       |

AS=amino acid sequence, which is a partial amino acid sequence of the LON T-4 peptide sequence (SEQ ID NO: 5)

8.3 "Southern Blot Hybridization" of Restriction Fragments of Plasmid pPRS2a

The DNA fragments obtained from pPRS2a after different restrictions (BamHI, SmaI, DraII, HindIII, EcoRI) which had been separated by agarose gel electrophoresis (0.6%) were transferred to nitro-cellulose by the known "Southern blot method" (Current Protocols in Molecular Biology, John Wiley and Sons, New York, 1987, Section 2.9 et seq.).

Also, the DNA oligomers were 3'-end-labelled with digoxigenin. Hybridization of the "Southern blots" followed the known procedure (in the abovementioned reference).

Hybridization with the nucleotide oligomer corresponding to the N-terminal protein sequence allowed a 1.44 kb SmaI/BamHI DNA fragment or a 1.52 kb DraII/BamHI DNA fragment to be identified on the hybrid plasmd pPRS2a.

8.4 Subcloning the Hydrolase Gene (Sad)

The 1.52 kb DraII/BamHI DNA fragment, or the 1.91 kb PstI/BamHI DNA fragment, which encodes the (R)-specific amidohydrolase from *Klebsiella oxytoca* PRS1K17 was inserted into equally digested vector DNA pBLUESCRIPT-KS+®.

The vector pBLUESCRIPT-KS+® containing the 1.52 kb DraII/BamHI DNA fragment was termed hybrid plasmid pPRS7. The vector pBLUESCRIPT-KS+® which contained the 1.91 kb PstI/BamHI DNA fragment was termed hybrid plasmid pPRS4.

8.5 Sequencing the Hydrolase Gene (Sad)

The 1.44 kb SmaI/BamHI fragment described further above under 8.3 was subjected to fluorescence sequencing using Sanger's dideoxy method (modified) with the aid of a laser fluorescence DNA sequenator. In this manner, the nucleotide sequence termed SEQ ID No. 1 was determined, from which the amino acid sequence for the amidohydrolase, which is shown separately under SEQ ID No. 2, is derived.

EXAMPLE 9

Determination of the Activity of the (R)-amidohydrolase Clones

The determination of the activity was carried out similarly to as described in Example 4.2.

The results with *E. coli*/pPRS1b and *E. coli*/pPRS2a as examples are shown in Table 2.

| | Hydrolase activity | | |
|---|---|---|---|
| Clone | (R)-amide g/l | (S)-amide g/l | Hours (h) |
| *E. coli* XL1-Blue MRF' ®/ pPRS1b (EcoRI clone) | 5.35 | 5.92 | 0 |
| *E. coli* XL1-Blue MRF' ®/ pPRS1b (EcoRI clone) | 0.00 ~Initial activity (37° C.) 0.29 g/l/ h/OD$_{650 \text{ nm}}$ | 5.84 | 4 |
| *E. coli* XL1-Blue MRF' ®/ pPRS2a (HindIII clone) | 5.66 | 5.92 | 0 |
| *E. coli* XL1-Blue MRF' ®/ pPRS2a (HindIII clone) | 0.00 ~Initial activity (37° C.) 0.13 g/l/ h/OD$_{650 \text{ nm}}$ | 6.20 | 8 |

EXAMPLE 10

Enzyme Purification and Enzyme Characterization 10.1 Enzyme Purification

During purification, the active fractions were determined by colorimetry. The activity of the cell-free extract and of the pure enzyme was then determined by the GC method. *Klebsiella oxytoca* PRS1 cells (200 ml, $OD_{650}=21$ in 100 mM phosphate buffer, pH 7.5) were disrupted by passing 3 times through a French press at 19000 psi (1309 bar). Benzonase (1 µl×30 ml extract$^{-1}$) was added, and the extract was then centrifuged for 15 minutes at 100000×g. The supernatant (2.94 mg×ml$^{-1}$) was heated for 10 minutes at 80° C., and the precipitated protein was then removed by centrifugation. The supernatant (170 ml, 0.83 mg×ml$^{-1}$) was applied to a HiLoad Q-Sepharose 26/10 chromatography column (Pharmacia) which had previously been equilibrated with 50 mM phosphate buffer (pH 7.5; buffer A). Unbound protein was eluted from the column using 130 ml of buffer A. Then, a linear gradient (500 ml; 1 M NaCl–0 M NaCl in buffer A) was established, the flow rate being 2.5 ml×min$^{-1}$. Fractions of 5 ml were collected and tested for activity. The most active fractions (30–37; 40 ml) were combined, concentrated to 7.5 ml by ultrafiltration, and the buffer was then exchanged for a 10 mM phosphate buffer (pH 7.5) by means of gel filtration chromatography (Sephadex G-25 M, PD 10, Pharmacia). The active fractions were then applied to a hydroxyapatite column (5 ml; Bio-Scale CHTI, BioRad) which had been equilibrated with a 10 mM phosphate buffer. Fractions of 1 ml were collected at a flow rate of 2.0 ml×min$^{-1}$ using a gradient (90 ml; 0.5 mM phosphate buffer–10 mM phosphate buffer pH 7.5) and tested for activity. Activity was shown by fractions 17–25 and 32–34. The protein ($M_r$ 37000) of fraction 19 and fractions 33 and 34 was pure according to SDS-PAGE. The protein of fraction 20 showed a purity of over 95%. Fractions 20–25 were combined, concentrated to 200 µl and then applied to a gel filtration chromatography column (Superose 12; Pharmacia). SDS-PAGE revealed that fractions 23–26 were pure.

10.2 Protein Sequencing

An N-terminal amino acid sequence was obtained by western blotting, and the protein was then digested with trypsin and the peptides were isolated by HPLC and sequenced.

| | |
|---|---|
| N terminus: | Met Lys Trp Leu Glu Glu Ser Ile Met Ala Lys Arg Gly Val Gly Ala Ser Arg Lys Pro (SEQ ID No. 3) |
| T3: | Val Tyr Trp Ser Lys (SEQ ID No. 4) |
| T4: | Lys Pro Val Thr His His Leu Thr Glu Glu Met Gln Lys (SEQ ID No. 5) |
| T5: | Tyr Thr Val Gly Ala Met Leu Asn Lys (SEQ ID No. 6) |
| T6A: | Met Glu Asn Ala Glu Asn Ile Met Ser Ile Gly Ser Ala Arg (SEQ ID No. 7) |
| T7: | Trp Leu Glu Glu Ser Ile Met Ala Lys (SEQ ID No. 8) |
| T8: | Met Pro Phe Leu Asn Pro Gln Asn Gly Pro Ile Met Val Asn Gly Ala Glu Lys (SEQ ID No. 9) |
| T9-2: | Asp Ala Phe Glu Gly Ala Ile Asn Ser Glu Gln Asp Ile Pro Ser Gln Leu Leu Lys (SEQ ID No. 10) |
| T9-2: | Glu Phe His Tyr Thr Ile Gly Pro Tyr Ser Thr Pro Val Leu Thr Ile Glu Pro Gly Asp Arg (SEQ ID No. 11) |
| T11: | Leu Phe Ile Gly Asp Ala His Ala Glu Gln Gly Asp Gly Glu Ile Glu Gly Thr Ala Val Glu Phe Ala (SEQ ID No. 12) |
| T13-1: | Gly Asp Val Leu Ala Val Tyr Ile Glu Ser Met Leu Pro Arg (SEQ ID No. 13) |
| T13-2: | Gly Val Asp Pro Tyr Gly Ile Glu Ala Met Ile Pro His Phe Gly Gly Leu Thr Gly Thr Asp Leu Thr Ala Met Leu Asn Asp Gln Leu Gln Pro Lys (SEQ ID No. 14) |

10.3 Enzyme Characterization

A heat-treated cell-free extract was employed for characterizing the amidase. Cells of *Klebsiella oxytoca* PRS1K17 (DSM 11623) ($OD_{650}=160$) were disrupted by passing through a French press at 19000 psi (1309 bar). Benzonase (1 µl×30 ml extract$^{-1}$) was added, and the extract was then centrifuged for 1 hour at 20000×g. The supernatant (approx. 20 mg×ml$^{-1}$ protein) was heated for 10 minutes at 70° C. and the precipitated protein was then removed by centrifugation. The supernatant (approx. 2.0 mg×ml$^{-1}$) was concentrated to 5.0 mg×ml$^{-1}$ protein and then stored at −20° C. The heat treatment removed approx. 90% of undesired protein. Up to a protein concentration of 0.5 mg×ml$^{-1}$, the reaction rate was in direct proportion to the protein concentration. A protein concentration of 0.2 mg×ml$^{-1}$ was therefore routinely employed in the tests. To determine the pH optimum, the concentration of (R,S)-2,2-HTFMPA (substrate) was 0.5% (32 mM) and the temperature was 40° C. The buffers listed in Table 4 were employed in the test.

TABLE 4

| Buffer | pH |
|---|---|
| 100 mM MES | 6.5 |
| 100 mM HEPES | 7.0; 7.5 |
| 50 mM phosphate buffer | 8.0; 8.5 |
| 50/100 mM Tris buffer | 8.0; 8.5 |
| 50/100 mM borate buffer | 9.0; 9.5 |
| 50/100 mM CAPS buffer | 10.0; 10.5; 11.0 |

The effect of the temperature on the reaction was determined in 100 mM CAPS buffer (pH 10.0) at a substrate concentration of 0.5% (32 mM). The effect of the substrate concentration was determined at 60° C. in 100 mM CAPS buffer (pH 10.0), and the effect of methanol at 40 and 60° C. at a substrate concentration of 1% (64 mM) in 100 mM CAPS buffer (pH 10.0). The $K_m$ value of the reaction was determined using the Enzfitter program of Biosoft.

FIG. 4 shows the pH optimum. The pH optimum is between 9.5 and 10.5 (100 mM CAPS buffer; substrate concentration 32 mM).

10.4 Enzyme Immobilization

Figure 1:
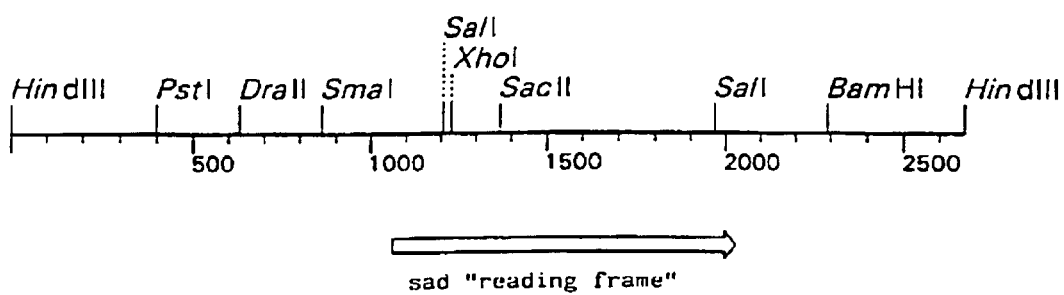
Figure 2:
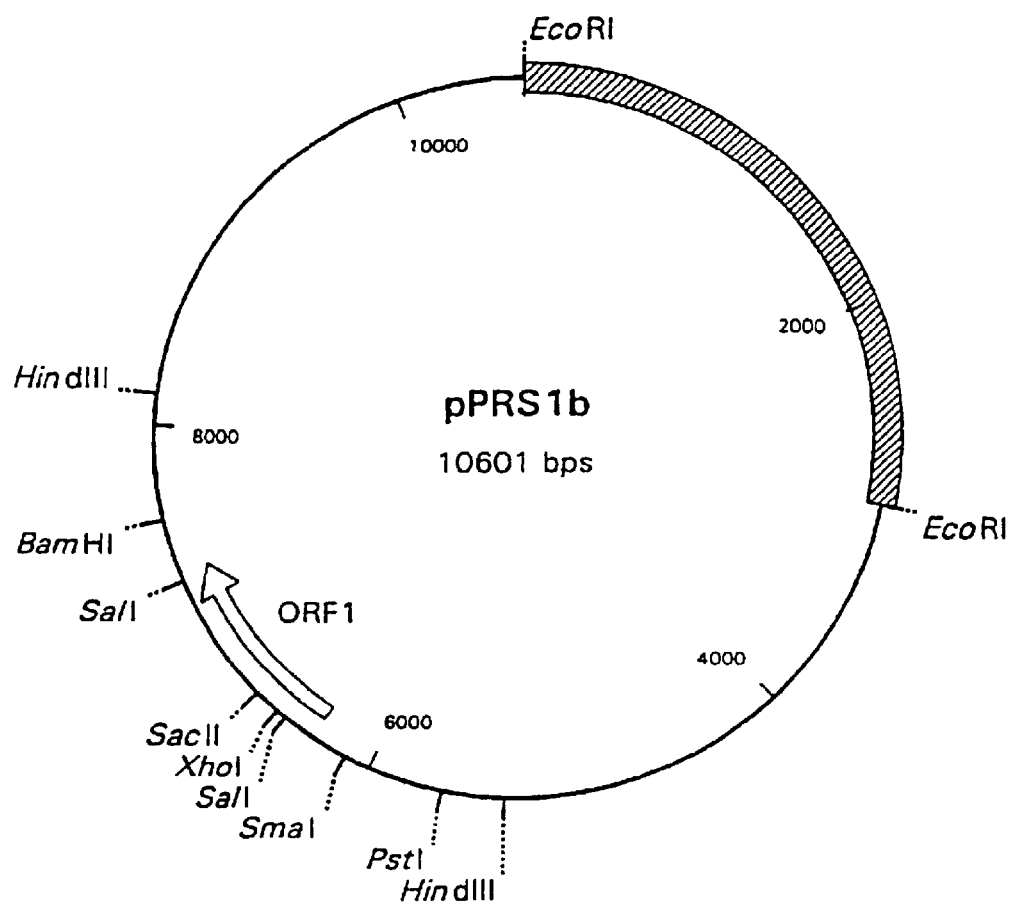
Figure 3:
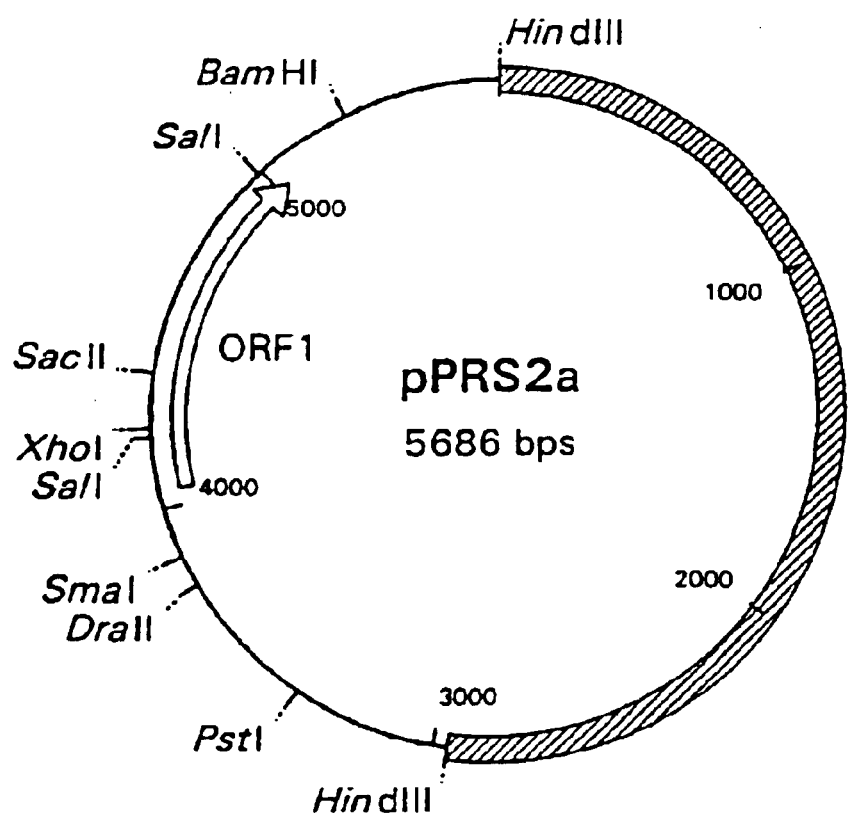
Figure 4:
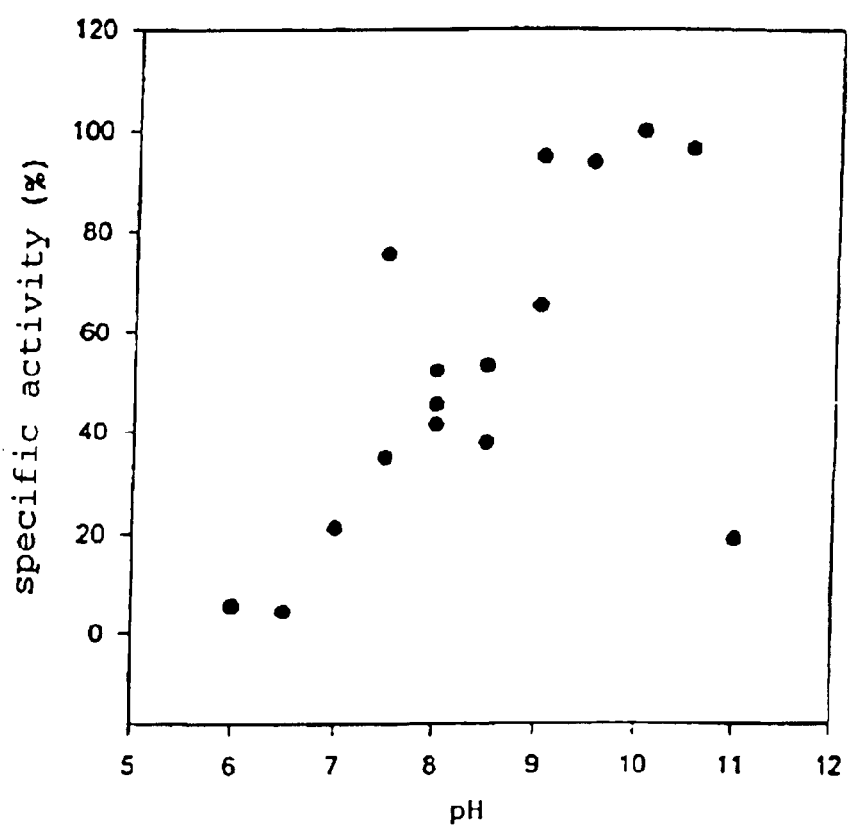
Figure 5:
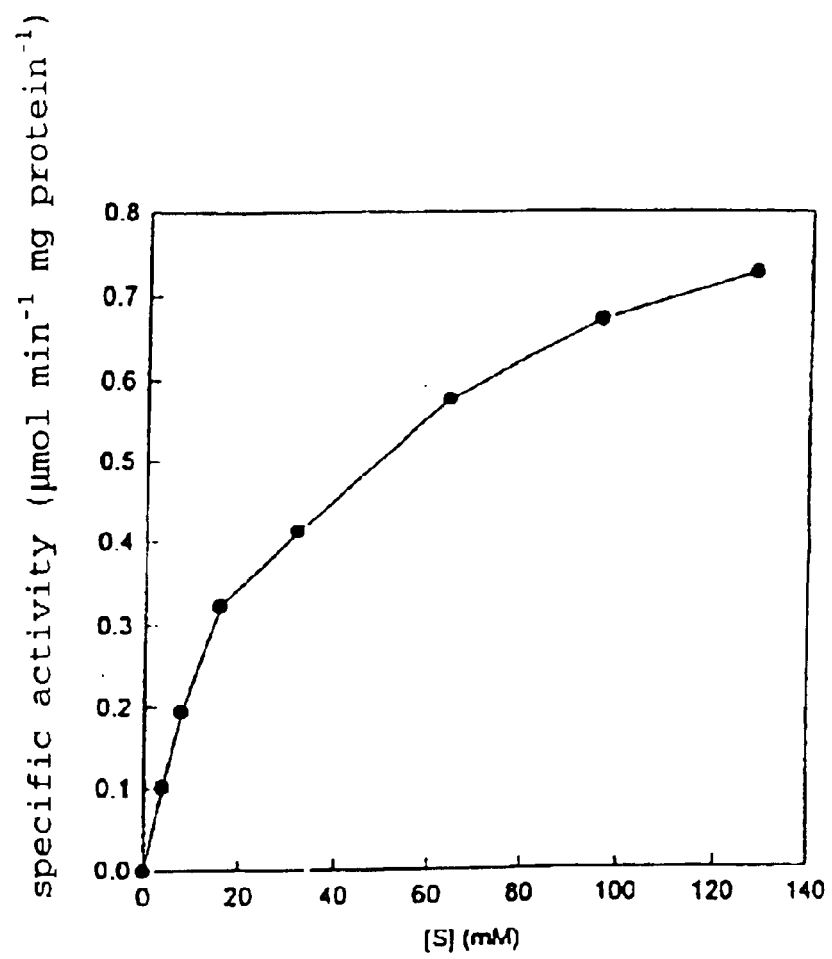
FIG. 5 shows the Michaelis-Menten kinetics. The $K_m$ value for (R)-2,2-HTFMPA is 32 mM (60° C. in 100 mM CAPS buffer, pH 10).
Figure 6:
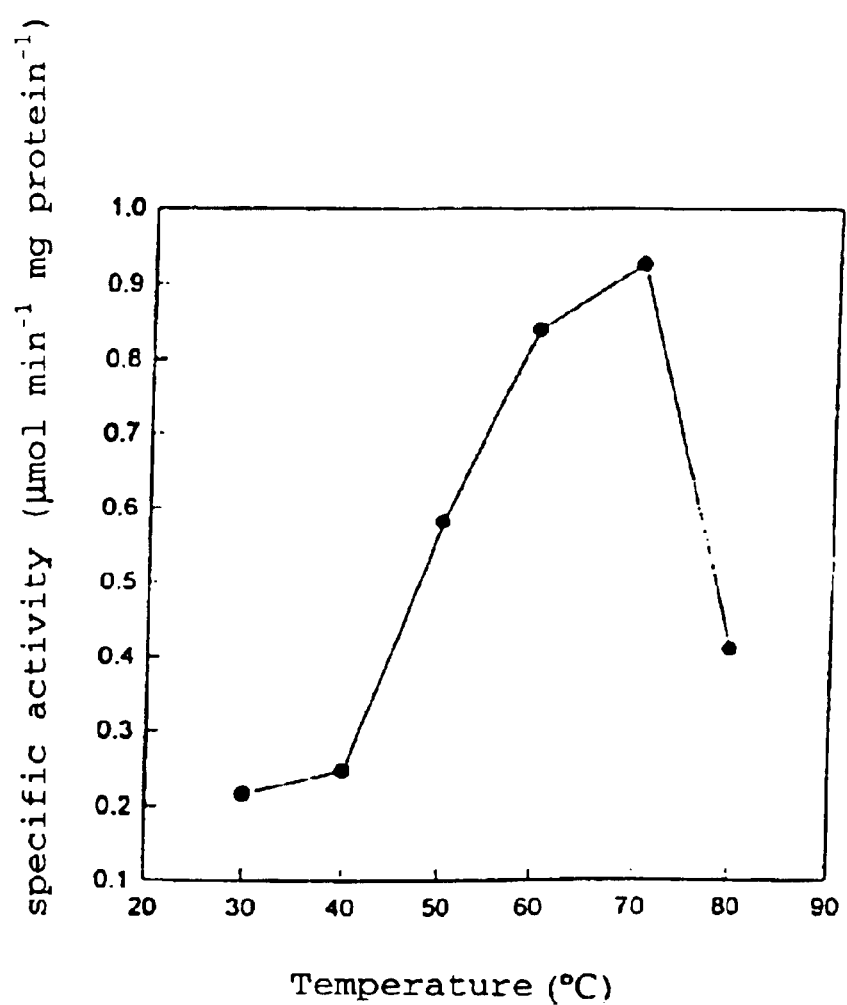
FIG. 6 shows the temperature optimum. The temperature optimum is 70° C. (100 mM CAPS buffer; substrate concentration 32 mM).
Figure 7:
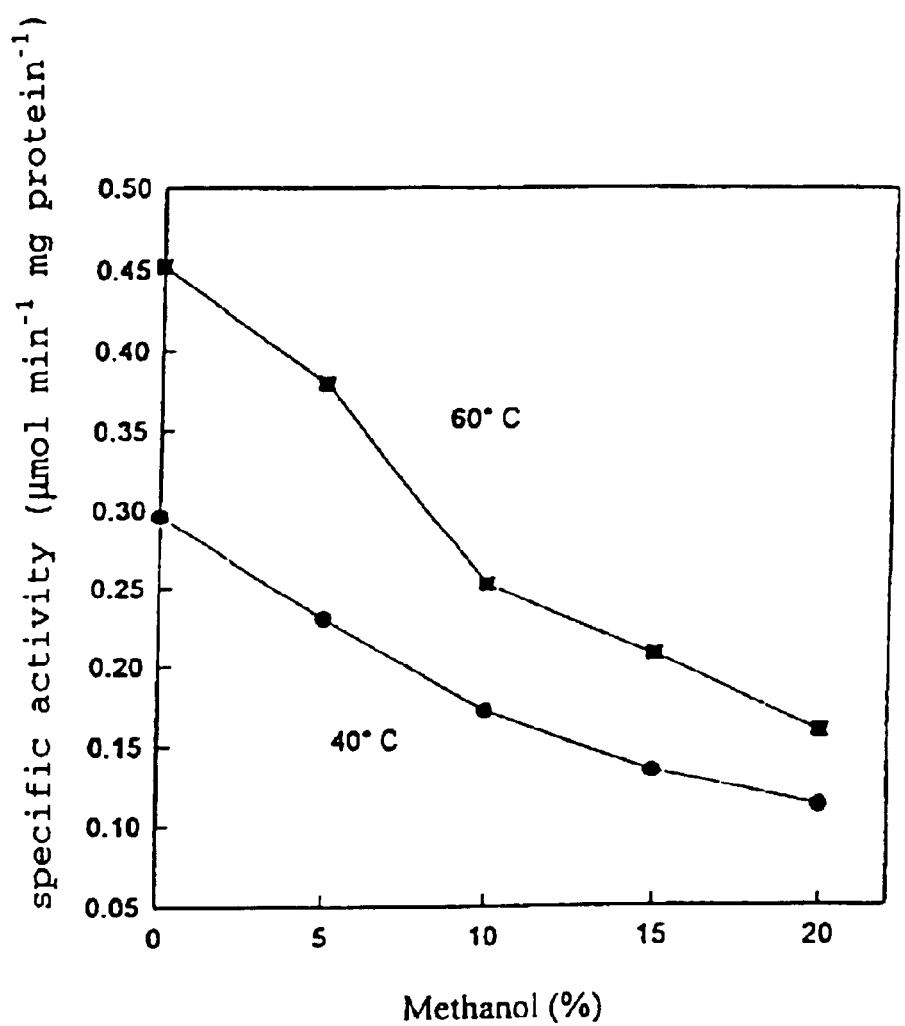
FIG. 7 shows the effect of methanol. Methanol concentrations of between 5 and 20% inhibit the reaction.

The heat-treated cell-free extract was immobilized using Eupergit C (Rbhm GmbH). To this end, Eupergit C (3.0 g) was added to 15 ml of heat-treated cell-free extract (protein concentration: 51 mg) in 1 M potassium phosphate buffer (pH 8.0). The mixture was incubated for 90 hours at room temperature with gentle stirring. The immobilized enzyme was filtered off and washed 4 times with 20 ml of 100 mM potassium phosphate buffer (pH 8.0). Support-bound enzyme (49 mg) gave 9.5 g of immobilized enzyme (fresh weight), which was stored in 100 mM potassium phosphate buffer (pH 10.0) at 4° C. To test the activity and stability of the immobilized enzyme, a small chromatography column was loaded with 5 g (25 mg of protein). A peristaltic pump (0.135 ml×min$^{-1}$) was used to circulate the substrate (100 ml 4% racemic amide in 100 mM CAPS buffer (pH 10)) between column and reservoir. The entire process was carried out in a water bath. At certain intervals, samples were taken for analysis. The enzyme was still active after 200 hours. Three biotransformations (each with 4 g of racemic substrate, the first having been carried out at 60° C. and the remaining two at 40° C.) gave a total of 6 g of (S)-amide. At the beginning of the reaction, immobilized enzyme (specific activity=47 µg×min$^{-1}$×mg protein$^{-1}$) was added at 60° C., which is comparable (41%) with non-immobilized enzyme (specific activity: 114 µg×min$^{-1}$×mg protein$^{-1}$).

What is claimed is:

1. A biologically pure culture of a microorganism wherein said microorganism utilizes propionamide of the formula:

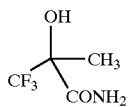

VI in the form of the racemate or of its optically active isomers as the sole nitrogen source; and wherein said microorganism is selected from the group consisting of the genus Arthrobacter, Bacillus, Klebsiella and Pseudomonas.

2. A biologically pure culture of a microorganism wherein said microorganism utilizes propionamide of the formula:

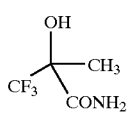

VI in the form of the racemate of its optically active isomers as the nitrogen source; and wherein said microorganism is selected from the group consisting of the species *Klebsiella oxytoca* PRS1 (DSM 11009), *Klebsiella oxytoca* PRS1K17 (DSM 11623), *Arthrobacter ramosus* ID-620 (DSM 11350), Bacillus sp, ID-621 (DSM 11351), *Klebsiella planticula* ID-624 (DSM 11354), *Klebsiella pneumoniae* ID-625 (DSM 11355) and Pseudomonas sp. (DSM 11010).

3. A cell extract derived from a biologically pure culture of a microorganism wherein said microorganism utilizes propionamide of the formula:

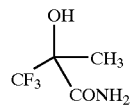

VI in the form of the racemate or of its optically active isomers as the sole nitrogen source; and wherein said microorganism is selected from the group consisting of the genus Arthrobacter, Bacillus, Klebsiella and Pseudomonas.

4. A cell extract derived from a biologically pure culture of a microorganism wherein said microorganism utilizes propionamide of the formula:

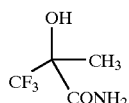

in the form of the racemate or of its optically active isomers as the sole nitrogen source; and wherein said microorganism is selected from the group consisting of the species *Klebsiella oxytoca* PRS1 (DSM 11009), *Klebsiella oxytoca* PRS1K17 (DSM 11623), *Arthrobacter ramosus* ID-420 (DSM 11350), Bacillus sp. ID-621 (DSM 11351), *Klebsiella planticula* ID-624 (DSM 11354), *Klebsiella pneumoniae* ID-625 (DSM 11355) and Pseudomonas sp. (DSM 11010).

5. A process for the preparation of (S)- or (R)-3,3,3-trifluoro-2-hydroxy-2-methylpropionic acid of the formula:

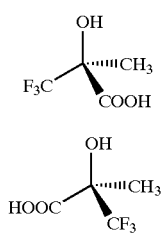

or of (R)- or (S)-3,3,3-trifluoro-2-hydroxy-2-methylpropionamide of the formula

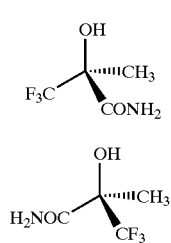

into a compound of the formula I, II, VII or VIII using:

(a) the microorganism of claim 1 or 2; or (b) the cell extract of claim 3 or 4.

6. The process of claim 5 further comprising the step of isolating a compound of the formula I, II, VII or VIII.

7. A process for the preparation of (R)-3,3,3-trifluoro-2-hydroxy-2-methylpropionic acid of the formula:

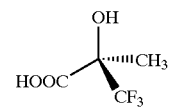

or of (S)-3,3,3-trifluoro-2-hydroxy-2-methyl-propionamide of the formula

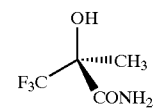

comprising converting propionamide of the formula

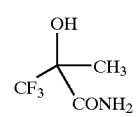

into the compound of the formula II utilizing the microorganism of claim 1 or 2.

8. The process of claim 7 further comprising the step of isolating the compound of formula II or formula VII.

9. The process of claim 7 wherein said microorganism contains a nucleic acid molecule encoding a polypeptide having aminohydrolase activity wherein said polypeptide hydrolyzes (R)-3,3,3-trifluoro-2-hydroxy-2-methylpropionamide of the formula:

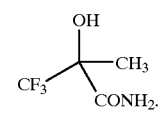

10. The process of claim 9 wherein said nucleic acid molecule encodes the amino acid sequence of SEQ ID NO:2.

11. The process of claim 9 wherein said nucleic acid molecule is selected from the group consisting of:

(a) a nucleic acid molecule comprising the sequence of SEQ ID NO:1;

(b) a nucleic acid molecule comprising the sequence complementary to SEQ ID NO:1; and (c) a nucleic acid molecule which hybridizes under stringent hybridization conditions to SEQ ID NO:1;

wherein said nucleic acid molecule encodes a polypeptide with stereospecific amidohydrolase activity.

12. The process of claim 7 wherein the microorganism is selected from the group consisting of the species *Klebsiella oxytoca* PRS1 (DSM 11009), *Klebsiella oxytoca* PRS1K17 (DSM 11623), *Klebsiella planticula* ID-624 (DSM 11354), and *Klebsiella pneumoniae* ID-625 (DSM 11355).

13. The process of claim 5 or 7 characterized in that the propionamide of the formula is prepared by converting, in a first step, trifluoroacetate of the formula

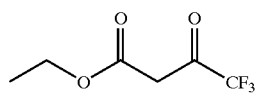  III into trifluoroacetone of the formula

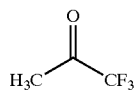  IV using a mineral acid, converting the former, in the second step, into the propionitrile of the formula

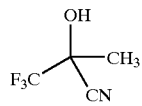  V using a cyanide, and converting the former, in the third step, into the propionamide of the formula

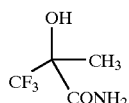  VI

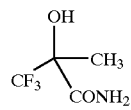  VI chemically using concentrated mineral acid.

14. The process of claim 13 wherein said mineral acid is selected from the group consisting of: sulphuric acid, phosphoric acid and nitric acid.

15. The process of claim 13 wherein said cyanide is an alkali metal cyanide.

16. The process of claims 5 or 7, characterized in that the (S)- or (R)-3,3,3-trifluoro-2-hydroxy-2-methylpropionamide of the formula

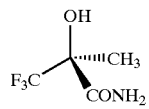  VII

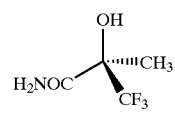  VIII is hydrolysed to the compound of the formula I or II (a) chemically in the presence of a base or (b) biologically utilizing the microorganism of claim 1 or 2.

* * * * *

SEQUENCE LISTING

<160> NUMBER OF SEQ ID NOS: 14

<210> SEQ ID NO 1
<211> LENGTH: 1442
<212> TYPE: DNA
<213> ORGANISM: Klebsiella oxytoca

<400> SEQUENCE: 1

```
cccgggaact ccatgtggcc gtgatcctgg tcgagcagga tattgcgatg atccagcggg      60
ccgcacagcg ctgtgcggta atggataaag gcctggttgt agaaacgctg acccaacaac     120
agctctctga tgatctttta atgcgtcgtc atctggctct gtaactaaac gctataaatt     180
acgtggagaa taacatatga aatggttgga agaatccatt atggccaaac gcggtgttgg     240
tgccggcgt aaaccggtaa cgcatcacct gacggaagaa atgcaaaaag agtttcatta     300
caccattggc ccttattcca cacccgtcct gaccatcgaa cccggtgacc ggattattgt     360
cgacactcga tgctttttg aaggtgctat caattcggaa caggatattc cgagccagtt     420
gctaaaaatg ccctttctca acccacaaaa cggaccgatc atggtcaatg cgcggagaa     480
aggtgatgtg ctcgctgtct atatcgaatc catgttgccc cgcggcgttg atccctacgg     540
catctgcgcc atgattccgc attttggcgg actgaccggg accgacctga cggccatgct     600
caatgatccg ctgccagaaa aggtgcgcat gattaaactc gacagtgaaa aggtctactg     660
gagcaaacgc catacgcttc cctataaacc ccatattggc accttgagcg tatcgccaga     720
aattgactca atcaattcac tgacgccaga caatcacggc gggaatatgg atgtgccgga     780
tataggacca gggagtatta cctatctgcc ggtacgtgcg cctggaggcc gcctgtttat     840
tggtgatgcc catgcttgtc agggtgatgg tgagatttgc gggaccgcag tagagtttgc     900
ctcaatcacc accatcaaag tcgatttgat caagaactgg cagctttcct ggccacgaat     960
ggagaatgcc gaaaatatta tgagtattgg cagtgcacgt ccgctggagg atgcgacgcg    1020
aattgcatat cgcgacttaa tttactggct ggtagaagac tttggcttcg acaatgggga    1080
tgcctacatg cttctgagtc aatgcggcaa agtgcggctg gcaacatgg tcgaccccaa    1140
atacaccgtt ggcgcgatgc tgaacaaaaa cctgttagtt tagtaggaat aactaaccgg    1200
tgaacattac ccggatgtag atcggggtaa tgtgtaagtt caaacaatcg ctattttaa     1260
cagctaaagc aggtgcatat ggggccagat acacccatca atattggttt actttactcc    1320
ttcagcggag tgacggcggc acaagagttg tcacaatggc gcggagcaac ccaggctatt    1380
gccgaaatta tcaaaatggc ggcatcaac ggcagaccac tcaatgcaat tcatttggat     1440
cc                                                                  1442
```

<210> SEQ ID NO 2
<211> LENGTH: 328
<212> TYPE: PRT
<213> ORGANISM: Klebsiella oxytoca

<400> SEQUENCE: 2

```
Met Lys Trp Leu Glu Glu Ser Ile Met Ala Lys Arg Gly Val Gly Ala
 1               5                  10                  15

Gly Arg Lys Pro Val Thr His His Leu Thr Glu Glu Met Gln Lys Glu
            20                  25                  30

Phe His Tyr Thr Ile Gly Pro Tyr Ser Thr Pro Val Leu Thr Ile Glu
        35                  40                  45
```

Pro Gly Asp Arg Ile Ile Val Asp Thr Arg Asp Ala Phe Glu Gly Ala
    50                  55                  60

Ile Asn Ser Glu Gln Asp Ile Pro Ser Gln Leu Leu Lys Met Pro Phe
65                  70                  75                  80

Leu Asn Pro Gln Asn Gly Pro Ile Met Val Asn Gly Ala Glu Lys Gly
                85                  90                  95

Asp Val Leu Ala Val Tyr Ile Glu Ser Met Leu Pro Arg Gly Val Asp
            100                 105                 110

Pro Tyr Gly Ile Cys Ala Met Ile Pro His Phe Gly Leu Thr Gly
            115                 120                 125

Thr Asp Leu Thr Ala Met Leu Asn Asp Pro Leu Pro Glu Lys Val Arg
    130                 135                 140

Met Ile Lys Leu Asp Ser Glu Lys Val Tyr Trp Ser Lys Arg His Thr
145                 150                 155                 160

Leu Pro Tyr Lys Pro His Ile Gly Thr Leu Ser Val Ser Pro Glu Ile
                165                 170                 175

Asp Ser Ile Asn Ser Leu Thr Pro Asp Asn His Gly Gly Asn Met Asp
            180                 185                 190

Val Pro Asp Ile Gly Pro Gly Ser Ile Thr Tyr Pro Leu Val Arg Ala
            195                 200                 205

Pro Gly Gly Arg Leu Phe Ile Gly Asp Ala His Ala Cys Gln Gly Asp
    210                 215                 220

Gly Glu Ile Cys Gly Thr Ala Val Glu Phe Ala Ser Ile Thr Thr Ile
225                 230                 235                 240

Lys Val Asp Leu Ile Lys Asn Trp Gln Leu Ser Trp Pro Arg Met Glu
                245                 250                 255

Asn Ala Glu Asn Ile Met Ser Ile Gly Ser Ala Arg Pro Leu Glu Asp
            260                 265                 270

Ala Thr Arg Ile Ala Tyr Arg Asp Leu Ile Tyr Trp Leu Val Glu Asp
            275                 280                 285

Phe Gly Phe Glu Gln Trp Asp Ala Tyr Met Leu Leu Ser Gln Cys Gly
    290                 295                 300

Lys Val Arg Leu Gly Asn Met Val Asp Pro Lys Tyr Thr Val Gly Ala
305                 310                 315                 320

Met Leu Asn Lys Asn Leu Leu Val
                325

<210> SEQ ID NO 3
<211> LENGTH: 20
<212> TYPE: PRT
<213> ORGANISM: Klebsiella oxytoca

<400> SEQUENCE: 3

Met Lys Trp Leu Glu Glu Ser Ile Met Ala Lys Arg Gly Val Gly Ala
1               5                   10                  15

Ser Arg Lys Pro
            20

<210> SEQ ID NO 4
<211> LENGTH: 5
<212> TYPE: PRT
<213> ORGANISM: Klebsiella oxytoca

<400> SEQUENCE: 4

Val Tyr Trp Ser Lys
1               5

-continued

```
<210> SEQ ID NO 5
<211> LENGTH: 13
<212> TYPE: PRT
<213> ORGANISM: Klebsiella oxytoca

<400> SEQUENCE: 5

Lys Pro Val Thr His His Leu Thr Glu Glu Met Gln Lys
  1               5                  10

<210> SEQ ID NO 6
<211> LENGTH: 9
<212> TYPE: PRT
<213> ORGANISM: Klebsiella oxytoca

<400> SEQUENCE: 6

Tyr Thr Val Gly Ala Met Leu Asn Lys
  1               5

<210> SEQ ID NO 7
<211> LENGTH: 14
<212> TYPE: PRT
<213> ORGANISM: Klebsiella oxytoca

<400> SEQUENCE: 7

Met Glu Asn Ala Glu Asn Ile Met Ser Ile Gly Ser Ala Arg
  1               5                  10

<210> SEQ ID NO 8
<211> LENGTH: 9
<212> TYPE: PRT
<213> ORGANISM: Klebsiella oxytoca

<400> SEQUENCE: 8

Trp Leu Glu Glu Ser Ile Met Ala Lys
  1               5

<210> SEQ ID NO 9
<211> LENGTH: 18
<212> TYPE: PRT
<213> ORGANISM: Klebsiella oxytoca

<400> SEQUENCE: 9

Met Pro Phe Leu Asn Pro Gln Asn Gly Pro Ile Met Val Asn Gly Ala
  1               5                  10                  15

Glu Lys

<210> SEQ ID NO 10
<211> LENGTH: 19
<212> TYPE: PRT
<213> ORGANISM: Klebsiella oxytoca

<400> SEQUENCE: 10

Asp Ala Phe Glu Gly Ala Ile Asn Ser Glu Gln Asp Ile Pro Ser Gln
  1               5                  10                  15

Leu Leu Lys

<210> SEQ ID NO 11
<211> LENGTH: 21
<212> TYPE: PRT
<213> ORGANISM: Klebsiella oxytoca

<400> SEQUENCE: 11

Glu Phe His Tyr Thr Ile Gly Pro Tyr Ser Thr Pro Val Leu Thr Ile
```

```
                1               5                  10                  15
Glu Pro Gly Asp Arg
                20

<210> SEQ ID NO 12
<211> LENGTH: 23
<212> TYPE: PRT
<213> ORGANISM: Klebsiella oxytoca

<400> SEQUENCE: 12

Leu Phe Ile Gly Asp Ala His Ala Glu Gln Gly Asp Gly Glu Ile Glu
 1               5                  10                  15

Gly Thr Ala Val Glu Phe Ala
                20

<210> SEQ ID NO 13
<211> LENGTH: 14
<212> TYPE: PRT
<213> ORGANISM: Klebsiella oxytoca

<400> SEQUENCE: 13

Gly Asp Val Leu Ala Val Tyr Ile Glu Ser Met Leu Pro Arg
 1               5                  10

<210> SEQ ID NO 14
<211> LENGTH: 33
<212> TYPE: PRT
<213> ORGANISM: Klebsiella oxytoca

<400> SEQUENCE: 14

Gly Val Asp Pro Tyr Gly Ile Glu Ala Met Ile Pro His Phe Gly Gly
 1               5                  10                  15

Leu Thr Gly Thr Asp Leu Thr Ala Met Leu Asn Asp Gln Leu Gln Pro
                20                  25                  30

Lys
```